US012297956B2

(12) United States Patent
Aubrey

(10) Patent No.: US 12,297,956 B2
(45) Date of Patent: May 13, 2025

(54) JOINT FOR A SUPPORT ARM AND SUPPORT ARM INCLUDING THE JOINT

(71) Applicant: MAKO Surgical Corp., Weston, FL (US)

(72) Inventor: Kathryn Elizabeth Aubrey, Parkland, FL (US)

(73) Assignee: MAKO Surgical Corp., Weston, FL (US)

( * ) Notice: Subject to any disclaimer, the term of this patent is extended or adjusted under 35 U.S.C. 154(b) by 13 days.

(21) Appl. No.: 18/383,933

(22) Filed: Oct. 26, 2023

(65) Prior Publication Data

US 2024/0142050 A1  May 2, 2024

Related U.S. Application Data

(60) Provisional application No. 63/419,447, filed on Oct. 26, 2022.

(51) Int. Cl.
*F16M 13/02* (2006.01)
*A61B 90/50* (2016.01)

(52) U.S. Cl.
CPC .......... *F16M 13/022* (2013.01); *A61B 90/50* (2016.02); *A61B 2090/508* (2016.02); *F16M 2200/024* (2013.01)

(58) Field of Classification Search
CPC .. F16M 13/02; F16M 2200/024; A61B 90/50; A61B 2090/508
USPC ...................................................... 248/274.1
See application file for complete search history.

(56) References Cited

U.S. PATENT DOCUMENTS

| 2,746,357 | A | 5/1956 | Dixon |
| 3,858,578 | A | 1/1975 | Milo |
| 5,609,565 | A | 3/1997 | Nakamura |
| 5,907,387 | A * | 5/1999 | Schwaegerle ............ A61B 3/00 351/200 |
| 6,663,563 | B1 | 12/2003 | Sharratt |
| 6,767,153 | B1 | 7/2004 | Holbrook |
| 7,182,731 | B2 | 2/2007 | Nguyen et al. |
| 8,622,186 | B2 | 1/2014 | Samie et al. |
| 9,333,142 | B2 * | 5/2016 | Schuerch, Jr. ......... F16M 11/06 |
| 10,216,070 | B2 * | 2/2019 | Wood ................. F16M 11/2092 |
| 10,259,126 | B1 * | 4/2019 | Kapczynski ........... A61B 34/30 |
| 10,543,051 | B2 | 1/2020 | Schena et al. |
| 10,624,708 | B2 * | 4/2020 | Hunter ................... A61B 34/30 |

(Continued)

*Primary Examiner* — Todd M Epps
(74) *Attorney, Agent, or Firm* — Howard & Howard Attorneys PLLC

(57) ABSTRACT

A support arm includes a first component, a second component, and a joint coupled to the first component and positionally supporting the second component. The joint includes a first one-way clutch, a second one-way clutch, and a locking mechanism. The locking mechanism is moveable between a first position wherein the first one-way clutch permits rotation of the second component in a first rotational direction and the second one-way clutch permits rotation of the second component in a second rotational direction to allow movement of the second component relative to the first component, and a second position wherein the first one-way clutch prevents rotation of the second component in the first rotational direction and the second one-way clutch prevents rotation of the second component in the second rotational direction to positionally lock the second component relative to the first component.

21 Claims, 10 Drawing Sheets

(56) References Cited

U.S. PATENT DOCUMENTS

| | | |
|---|---|---|
| 11,020,198 B2 | 6/2021 | Johnson |
| 11,224,495 B2 * | 1/2022 | Reinke .................... F16H 21/44 |
| 2012/0010629 A1 | 1/2012 | Mire et al. |
| 2012/0241274 A1 | 9/2012 | Lloyd |
| 2014/0314538 A1 * | 10/2014 | Carter .................... A61B 90/50 |
| | | 414/744.3 |
| 2021/0171206 A1 | 6/2021 | Holstine et al. |

* cited by examiner

JOINT FOR A SUPPORT ARM AND SUPPORT ARM INCLUDING THE JOINT

CROSS-REFERENCE TO RELATED APPLICATIONS

The subject application claims priority to and all the benefits of U.S. Provisional Patent App. No. 63/419,447, filed Oct. 26, 2022, the contents of which is hereby incorporated by reference in its entirety.

BACKGROUND

Conventional support arms known in the art are used to support a variety of components or tools. Often, these components or tools are required to be moved into position relative to a target site on which the components or tool interact, and then subsequently fixed in position relative to the target site. To move the components or tools into position relative to the target site and then subsequently fix the components or tools in position, the support arms known in the art are required to be selectively positionally locked in place through a locking mechanism. However, these conventional locking mechanisms often result in the support arm being large, unwieldy, and both difficult to maneuver into position and difficult to accurately fix into position relative to the target site. More specifically, these conventional locking mechanisms typically have large diameters, thus resulting in the support arms having large diameters. Moreover, these prior locking mechanisms are often complex, costly, and both difficult to operate and difficult to maintain.

As such, there remains a need to provide an improved support arm.

SUMMARY

According to a first aspect, a support arm is provided that includes a first component extending along an axis, a second component spaced from the first component, and a joint coupled to the first component and positionally supporting the second component. The joint includes a first one-way clutch configured to selectively prevent rotation of the second component relative to the first component in a first rotational direction. The joint also includes a second one-way clutch configured to selectively prevent rotation of the second component relative to the first component in a second rotational direction opposite the first rotational direction. The joint further includes a locking mechanism moveable between a first position and a second position. In the first position, the first one-way clutch permits rotation of the second component relative to the first component in the first rotational direction and the second one-way clutch permits rotation of the second component relative to the first component in the second rotational direction to allow movement of the second component relative to the first component. In the second position, the first one-way clutch prevents rotation of the second component relative to the first component in the first rotational direction and the second one-way clutch prevents rotation of the second component relative to the first component in the second rotational direction to positionally lock the second component relative to the first component.

According to a second aspect, a joint is provided for a support arm, the joint comprising: a first one-way clutch extending about an axis and configured to selectively prevent rotation of a second component relative to a first component in a first rotational direction; a second one-way clutch spaced from the first one-way clutch along the axis, the second one-way clutch configured to selectively prevent rotation of the second component relative to the first component in a second rotational direction opposite the first rotational direction; and a locking mechanism moveable between, a first position where the first one-way clutch is configured to permit rotation of the second component relative to the first component in the first rotational direction and the second one-way clutch is configured to permit rotation of the second component relative to the first component in the second rotational direction to allow movement of the second component relative to the first component; and a second position where the first one-way clutch is configured to prevent rotation of the second component relative to the first component in the first rotational direction and the second one-way clutch is configured to prevent rotation of the second component relative to the first component in the second rotational direction to positionally lock the second component relative to the first component.

According to a third aspect, a support arm is provided comprising: a first component extending along an axis; a second component spaced from the first component; and a joint coupled to the first component and positionally supporting the second component, the joint having an inner joint surface defining a joint interior, and the joint including a clutch assembly configured to selectively prevent rotation of the second component relative to the first component, wherein the clutch assembly includes, a shaft extending along the axis and moveable between a first shaft position and a second shaft position spaced from the first shaft position along the axis; a center structure defining a longitudinal bore extending along the axis for receiving the shaft, and defining a transverse bore extending radially away from the axis; a plunger disposed in the transverse bore of the center structure, the plunger moveable between a first plunger position and a second plunger position spaced radially inward from the first plunger position; and a moveable member coupled to the center structure and moveable between, a first member position associated with the plunger in the first plunger position, and a second member position associated with the plunger in the second plunger position, wherein the moveable member is in contact with the inner joint surface of the joint in the second member position to positionally lock the second component relative to the first component.

According to a fourth aspect, a joint of the support arm of the third aspect is provided.

BRIEF DESCRIPTION OF THE DRAWINGS

Other advantages will be readily appreciated, as the same becomes better understood by reference to the following detailed description when considered in connection with the accompanying drawings wherein.

DETAILED DESCRIPTION

Figure 1:
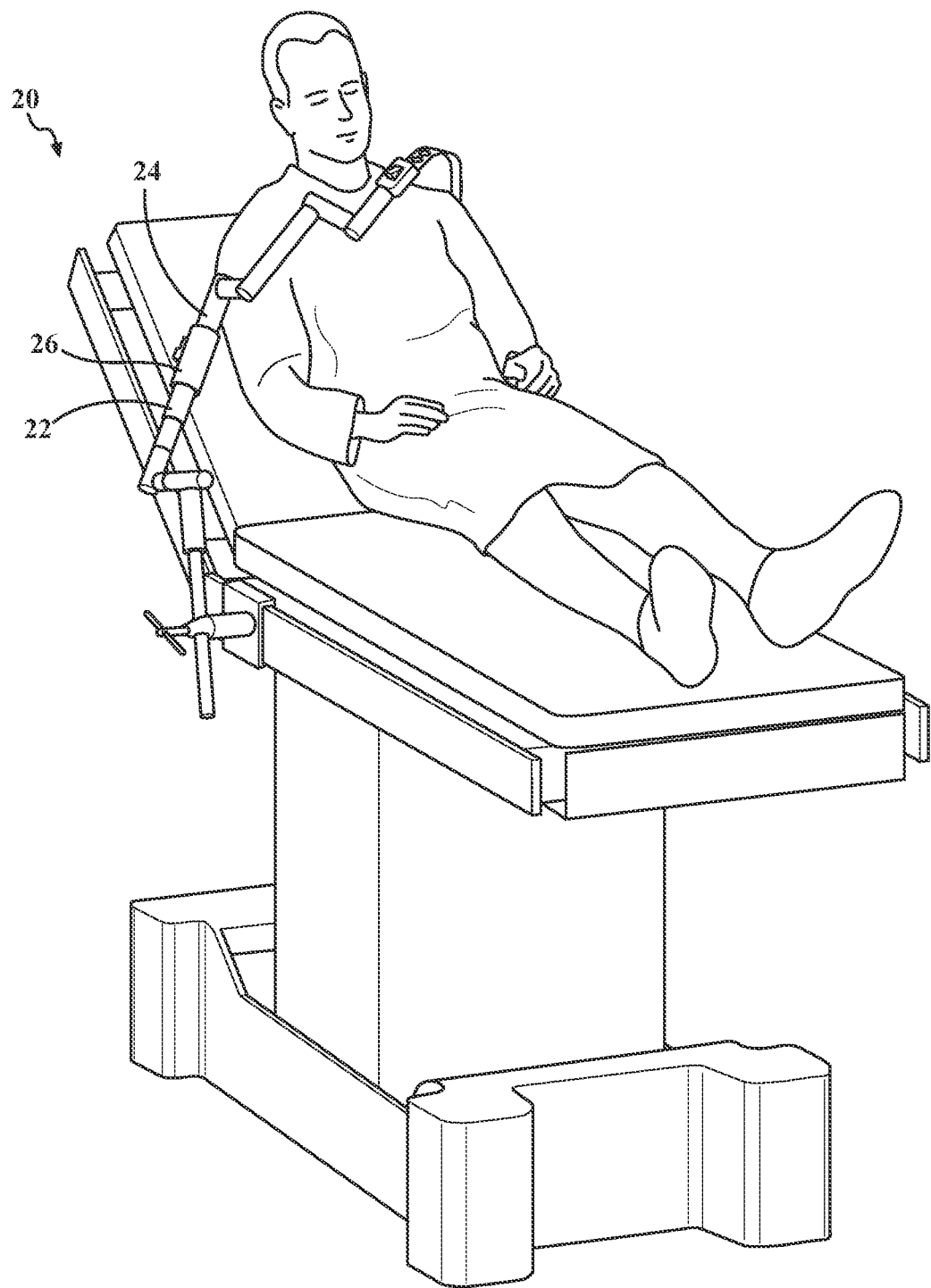
FIG. 1 is a perspective view of a support arm.

With reference to the Figures, wherein like numerals indicate like parts throughout the several views, a support arm 20 includes a first component 22 extending along an axis A1, a second component 24 spaced from the first component 22, and a joint 26 coupled to the first component 22 and positionally supporting the second component 24. The second component 24 may be positionally supported only by the joint 26 and the first component, and the second component 24 need not be supported elsewhere. The joint 26 includes a first one-way clutch 28 configured to selectively prevent rotation of the second component 24 relative to the first component 22 in a first rotational direction RD1. The first rotational direction RD1 may be either clockwise and counter-clockwise. The joint 26 also includes a second one-way clutch 30 configured to selectively prevent rotation of the second component 24 relative to the first component 22 in a second rotational direction RD2 opposite the first rotational direction RD1. As such, the second rotational direction RD2 may be the other of clockwise and counter-clockwise relative to the first rotational direction RD1.

Figure 2:
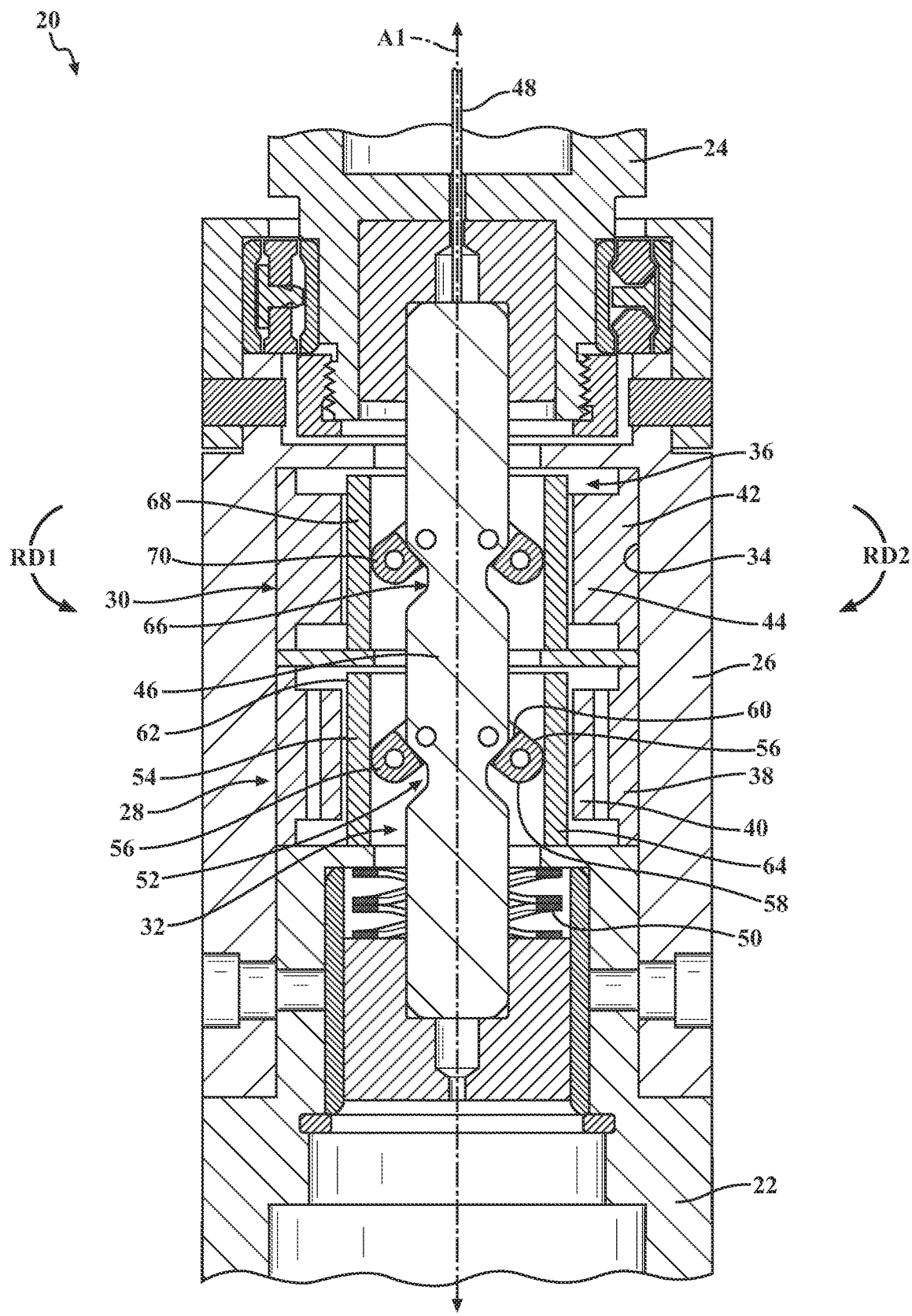
FIG. 2 is a cross-sectional view of the support arm, with the support arm including a locking mechanism in a first position.
Figure 3:
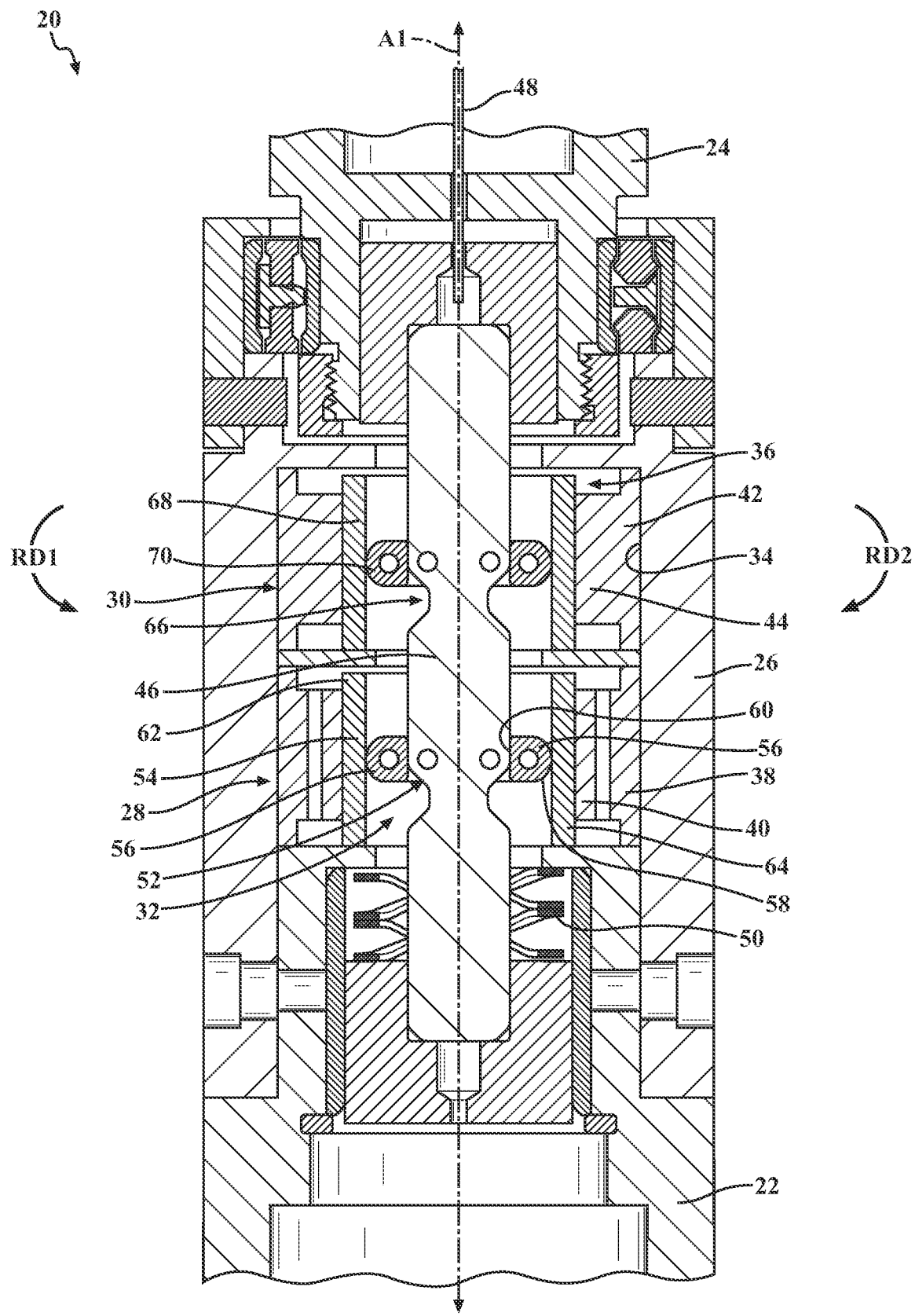
FIG. 3 is a cross-sectional view of the support arm, with the locking mechanism in the second position.
Figure 4:
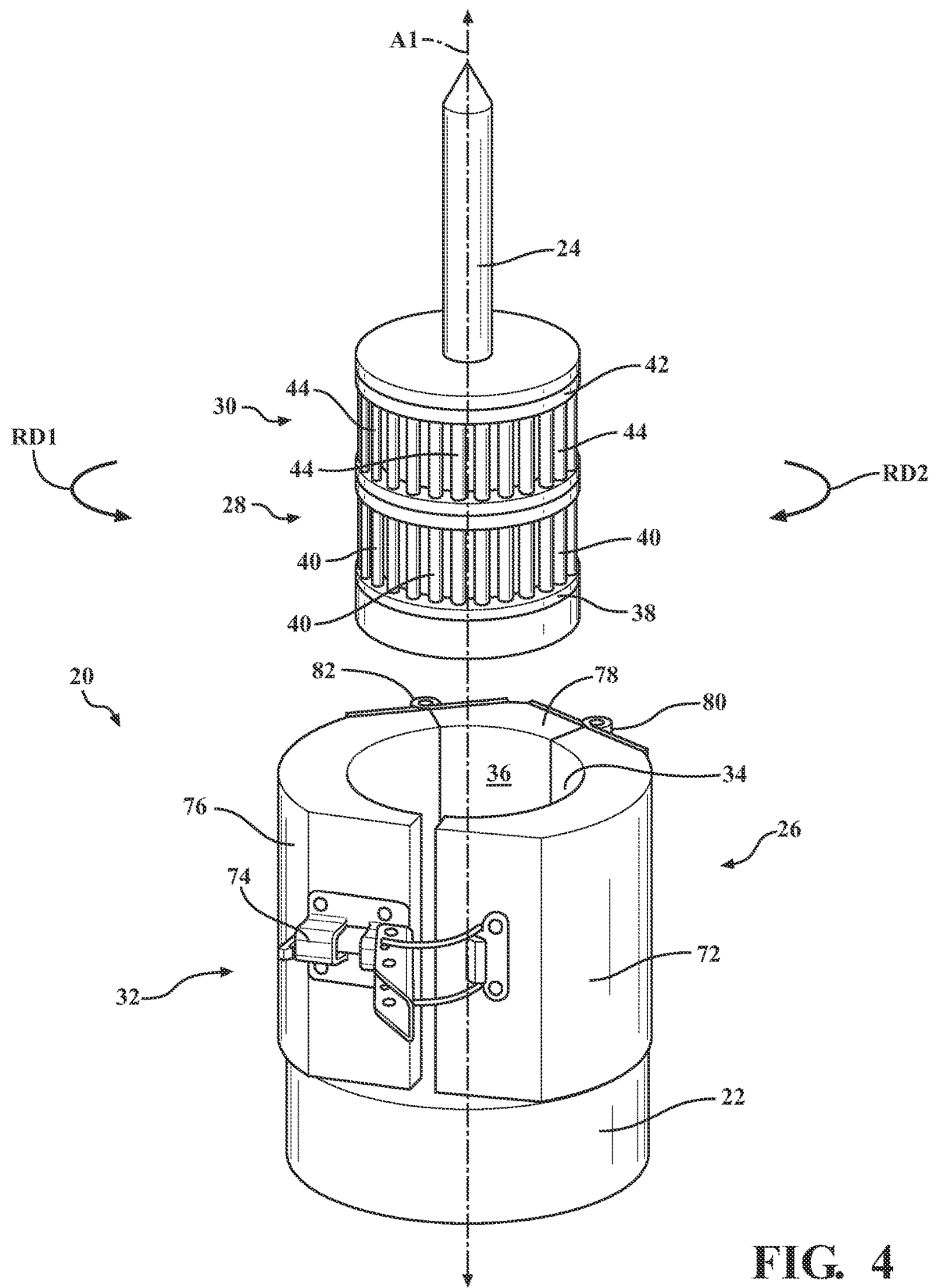
FIG. 4 is a perspective view of another implementation of the support arm, with the locking mechanism in the first position.
Figure 5:
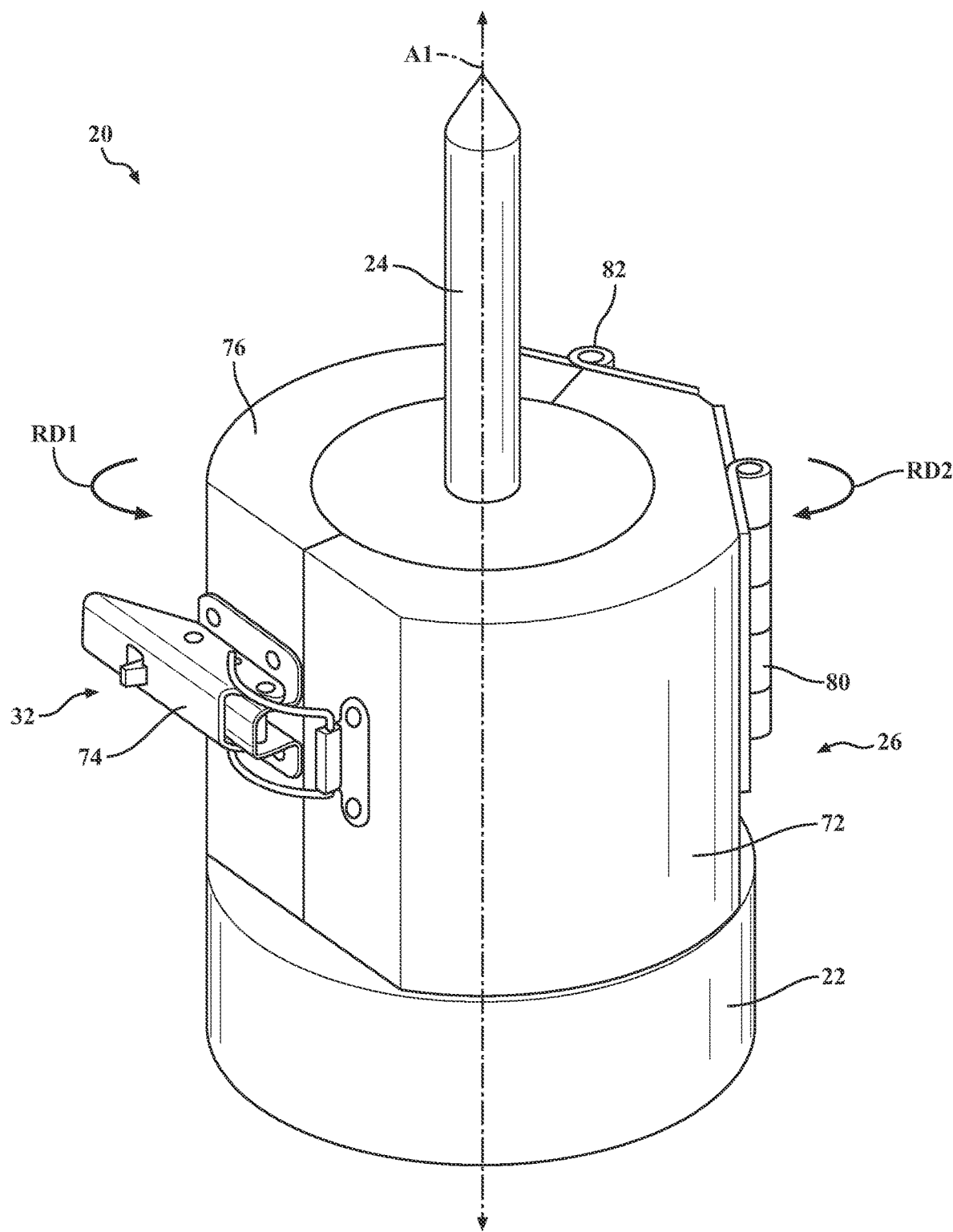
FIG. 5 is a perspective view of the implementation of the support arm shown in FIG. 4, with the locking mechanism in the second position.
Figure 6:
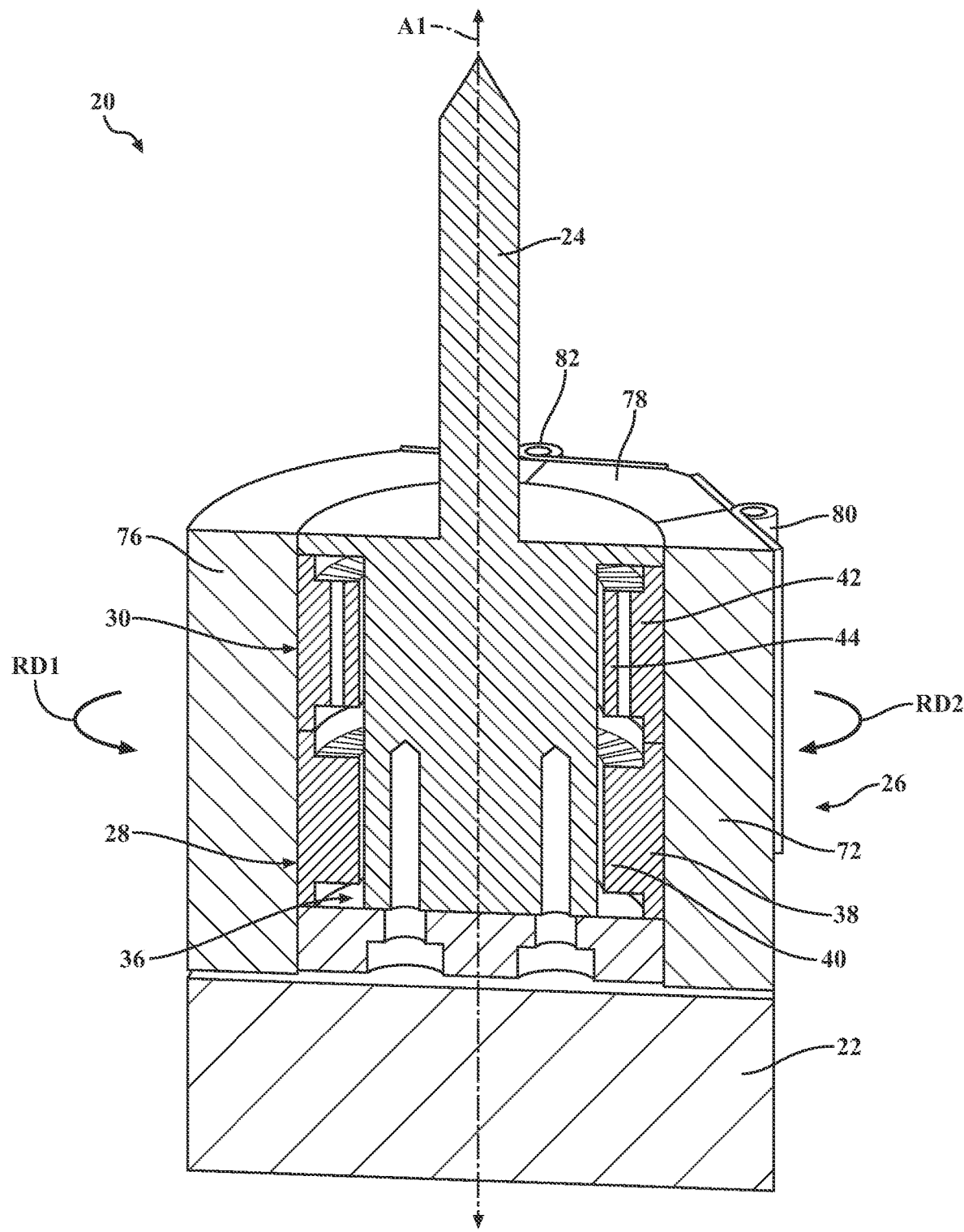
FIG. 6 is a cross-sectional view of the implementation of the support arm shown in FIG. 5.

The joint 26 further includes a locking mechanism 32 moveable between a first position and a second position. In the first position, as shown in FIGS. 2 and 4, the first one-way clutch 28 permits rotation of the second component 24 relative to the first component 22 in the first rotational direction RD1 and the second one-way clutch 30 permits rotation of the second component 24 relative to the first component 22 in the second rotational direction RD2 to allow movement of the second component 24 relative to the first component 22. In the second position, as shown in FIGS. 3, 5, and 6, the first one-way clutch 28 prevents rotation of the second component 24 relative to the first component 22 in the first rotational direction RD1 and the second one-way clutch 30 prevents rotation of the second component 24 relative to the first component 22 in the second rotational direction RD2 to positionally lock the second component 24 relative to the first component 22.

The locking mechanism 32 results in the support arm 20 being manageably sized, agile, and both easy to maneuver into position and easy to accurately positionally lock. Moreover, the locking mechanism 32 is relatively simple, inexpensive, and both easy to operate and easy to maintain.

Furthermore, the design of the locking mechanism 32 enables the support arm to be rotationally locked in any number of infinite positions, thereby improving usability and customization of the arm 20 for the user.

Although not required, the first one-way clutch 28 and the second one-way clutch 30 may be spaced from one another along the axis A1, as shown in FIGS. 2-4 and 6. Alternatively, the first one-way clutch 28 may be radially spaced from the second one-way clutch 30 relative to the axis A1. Moreover, the first one-way clutch 28 and the second one-way clutch 30 may be integrated into a single clutch assembly, such as but not limited to a selectable one-way clutch (SOWC), also known as a multi-mode clutch.

The first one-way clutch 28 and the second one-way clutch 30 may be configured to permit the second component 24 to be positionally locked in any rotational orientation relative to the first component 22. More specifically, the first one-way clutch 28 and the second one-way clutch 30 may be configured to permit the second component 24 to be positionally locked in any rotational orientation. In other words, the second component 24 can be positionally locked in any one of virtually infinite rotational orientations (e.g., about a 360-degree range of motion). In other examples, the first one-way clutch 28 and the second one-way clutch 30 may positionally lock the second component 24 in any one of a predefined or fixed number of discrete rotational orientations.

The joint 26 may have an inner joint surface 34 defining a joint interior 36. The first one-way clutch 28 may be disposed within the joint interior 36 of the joint 26. Moreover, the second one-way clutch 30 may be disposed within the joint interior 36 of the joint 26. Moreover, the first one-way clutch 28 may include a first race 38 and a first plurality of moveable members 40 coupled to the first race 38. The second one-way clutch 30 may include a second race 42 and a second plurality of moveable members 44 coupled to the second race 42. Although not required, the first race 38 and the second race 42 may be spaced from one another along the axis A1. In one aspect, the first plurality of moveable members 40 are configured to contact the inner joint surface 34 of the joint 26. In another aspect, the first plurality of moveable members 40 are configured to contact an intervening component that is fixed to the joint 26.

The joint 26 may be fixed relative to the first component 22 or may be fixed relative to the second component 24. As such, the first one-way clutch 28 may be fixed relative to the first component 22 or may be fixed relative to the second component 24. More specifically, the first race 38 of the first one-way clutch 28 may be fixed relative to the first component 22 or may be fixed relative to the second component 24, and the second race 42 of the second one-way clutch 30 may be fixed relative to the first component 22 or may be fixed relative to the second component 24. The first one-way clutch 28, including the first race 38, need not be fixed relative to the same component that the second one-way clutch 30, including the second race 42, is fixed to. In other words, the first one-way clutch 28, optionally including the first race 38, may be fixed relative to the first component 22 and the second one-way clutch 30, optionally including the second race 42, may be fixed relative to the second component 24 or vice versa.

The first race 38 and the second race 42 may both be an insert element, as a non-limiting example Insert Element FE 422 Z from GMN. The first and second one-way clutches 28, 30 may each include a biasing mechanism, such as but not limited to a tension spring or a meander spring, coupled to the first and second pluralities of moveable members 40, 44 to preload the first and second pluralities of moveable members 40, 44. Each tension spring is disposed circumferentially about either the first plurality of moveable members 40 or the second plurality of moveable members 44 to provide the first or second pluralities of moveable members 40, 44 with a collective spring tension. Moreover, each meander spring may be coupled to at least one of the moveable members 40, 44 of the first or second pluralities of moveable members 40, 44 to provide each of the moveable members 40, 44 individually with an independent spring tension.

Alternatively, the first race 38 may be further defined as a first outer race rotationally fixed relative to the joint 26 such that the first plurality of moveable members 40 are spaced radially inward relative to the first outer race, and the second race 42 may be further defined as a second outer race rotationally fixed relative to the joint 26 such that the second plurality of moveable members 44 are spaced radially inward relative to the second outer race. It is to be appreciated that the first outer race may be rotationally fixed relative to the joint 26 without being directly fixed to the joint 26 (e.g., without being fixed directly to the inner joint surface 34), and instead may be fixed to any number of intervening components which are rotationally fixed to the joint 26. It is also to be appreciated that the second outer race may be rotationally fixed relative to the joint 26 without being directly fixed to the joint 26 (e.g., without being fixed directly to the inner joint surface 34), and instead may be fixed to any number of intervening components which are rotationally fixed to the joint 26.

In another alternative, the first race 38 may be further defined as a first inner race rotationally fixed relative to one of the first component 22 and the second component 24 such that the first plurality of moveable members 40 are spaced radially outward relative to the first inner race. The first inner race may be rotationally fixed relative to the first component 22 or relative to the second component 24. Moreover, it is to be appreciated that the first inner race may be rotationally fixed relative to one of the first component 22 and the second component 24 without being directly fixed to one of the first component 22 and the second component 24, and instead may be fixed to any number of intervening components which are rotationally fixed to one of the first component 22 and the second component 24.

The second race 42 may be further defined as a second inner race rotationally fixed relative to one of the first component 22 and the second component 24 such that the second plurality of moveable members 44 are spaced radially outward relative to the second inner race. The second inner race may be rotationally fixed relative to the first component 22 or relative to the second component 24. Moreover, it is to be appreciated that the second inner race may be rotationally fixed relative to one of the first component 22 and the second component 24 without being directly fixed to one of the first component 22 and the second component 24, and instead may be fixed to any number of intervening components which are rotationally fixed to one of the first component 22 and the second component 24.

Further, the first plurality of moveable members 40 may be sprags and the second plurality of moveable members 44 may be sprags. The first and second pluralities of moveable members 40, 44 being sprags permit the second component 24 to be positionally locked in any rotational orientation relative to the first component 22. More specifically, the sprags permit the second component 24 to be positionally locked in any rotational orientation (e.g., any one of virtually infinite rotational orientations about a 360-degree range of motion). In other examples, the sprags could enable positional locking of the second component 24 in any one of a fixed or predefined number of discrete rotational orientations.

Alternatively, the first plurality of moveable members 40 may be struts and the second plurality of moveable members 44 may be struts. The first and second pluralities of moveable members 40, 44 being struts may increase the torque required to overcome pluralities of moveable members 40, 44, thus increasing the resiliency of the fixed position of the support arm 20. The first and second pluralities of moveable members 40, 44 being struts may limit the positional locking of the second component 24 to a fixed number of discrete rotational orientations.

The first component 22 may be rotationally fixed to the joint 26 and the second component 24 may be selectively rotatable relative to the joint 26, optionally supported by bearings such as ball bearings. Alternatively, the first component 22 may be selectively rotatable relative to the joint 26, optionally supported by bearings such as ball bearings, and the second component 24 may be rotationally fixed to the joint 26. In one aspect, the first component 22 is a first link and the second component is a second link. Alternatively, in another aspect, the first component 22 is a first link and the second component 24 is at least one chosen from an end effector, a tool, an array, a retractor (e.g., for shoulder surgery), and an attachment interface. In other words, the second component 24 may be one or more of the end effector, the tool, the array, the retractor, and the attachment interface.

Although not required, at least one of the first component 22 and the second component 24 may be disposed at least partially in the joint interior 36 of the joint 26. In other words, the first component 22 may be disposed at least partially in the joint interior 36 of the joint 26, the second component 24 may be disposed at least partially in the joint interior 36 of the joint 26, or both the first component 22 and the second component 24 may be disposed at least partially in the joint interior 36 of the joint 26.

As shown in FIGS. 2 and 3, the locking mechanism 32 may further include a shaft 46 disposed at least partially in the joint interior 36 of the joint 26. The shaft 46 may extend along the axis A1 and is moveable along the axis A1 between a first shaft position such that the locking mechanism 32 is in the first position and a second shaft position such that the locking mechanism 32 is in the second position. The first shaft position is shown in FIG. 2 and the second shaft position is shown in FIG. 3. The shaft 46 may be rotationally fixed relative to either of the first component 22, the second component 24, or neither the first component 22 or the second component 24.

Moreover, the locking mechanism 32 may further include a cable 48 coupled to the shaft 46. The cable 48 is configured to be manipulated by an operator to linearly translate the shaft 46 from the second shaft position toward the first shaft position, including but not limited to all of the way to the first shaft position. The operator may manipulate the cable 48 manually or through use of an actuator such as but not limited to a solenoid. The cable 48 may be manipulated through a direct force exerted by the operator on the cable, or the locking mechanism 32 may include a button operatively attached to the cable 48 and the operator may engage the button to indirectly exert a force on the cable 48 to manipulate the cable 48.

The locking mechanism 32 may further include a biasing mechanism 50 coupled to the shaft 46 and configured to bias the shaft 46 toward the second shaft position, including but not limited to all of the way to the second shaft position. The biasing mechanism 50 may be a spring, such as but not limited to a wave spring (e.g., a single wave spring, a multiple wave spring), a coil spring (e.g., a compression spring, a helical spring), a disc spring (e.g., a Belleville spring, a conical spring), or a slotted disk spring, among other possibilities.

As such, as a result of the biasing mechanism 50 being configured to bias the shaft 46 toward the second shaft position, it is to be appreciated that the locking mechanism 32 as shown in FIG. 3 is normally in the second position and the second component 24 is normally positionally locked relative to the first component 22. To reposition the support arm 20, the operator may manipulate the cable 48, moving the shaft 46 from the second shaft position to the first shaft position, thus moving the locking mechanism 32 to the first position and allowing movement of the second component 24 relative to the first component 22.

The shaft 46 may define a groove 52, as shown in FIGS. 2 and 3. The locking mechanism 32 may further include a sleeve 54 disposed between the shaft 46 and the first one-way clutch 28. Further, the locking mechanism 32 may include a contactable component 56 coupled to the shaft 46. The contactable component 56 is moveable between a first component position, as shown in FIG. 2, and a second component position, as shown in FIG. 3. In the first component position, the contactable component 56 is disposed at least partially in the groove 52 of the shaft 46 such that the first one-way clutch 28 permits rotation of the second component 24 in the first rotational direction RD1. In the second component position, the contactable component 56 is in contact with the sleeve 54 such that the first one-way clutch 28 prevents rotation of the second component 24 in the first rotational direction RD1.

The sleeve 54 may be moveable between a first sleeve position associated with the contactable component 56 in the first component position and a second sleeve position associated with the contactable component 56 in the second component position. The second sleeve position may be spaced radially outward from the first sleeve position. In other words, the sleeve 54 in the second sleeve position may be spaced radially outward from the sleeve 54 in the first sleeve position. Furthermore, the sleeve 4 may be in contact with the first one-way clutch 28 in the second sleeve position. Contact between the sleeve 54 and the first one-way clutch 28 assists in preventing rotation of the second component 24.

The contactable component 56 may include a rounded surface 58 and a flat surface 60. The flat surface 60 of the contactable component 56 may be disposed at least partially in the groove 52 defined by the shaft 46 in the first component position. The flat surface 60 of the contactable component 6 may be approximately parallel with the shaft 46 in the second component position, and the rounded surface 58 may be in contact with the sleeve 54 in the second component position to move the sleeve 54 radially outward to the second sleeve position.

Moreover, the sleeve 54 may have a first sleeve portion 62 and a second sleeve portion 64. The first sleeve portion 62 and the second sleeve portion 64 of the sleeve 54 may be separate components. The first sleeve portion 62 and the second sleeve portion 64 of the sleeve 54 may both extend approximately halfway circumferentially about the axis A1. In a non-limiting example, the first sleeve portion 62 and the second sleeve portion 64 of the sleeve 54 may be separated from one another by one or more gaps in the second sleeve position, and the first sleeve portion 62 and the second sleeve portion 64 of the sleeve 54 may be in contact with one another in the first sleeve position. The gaps between the first sleeve portion 62 and the second sleeve portion 64 of the sleeve 54 may result in the sleeve 54 in the second sleeve position being spaced radially outward from the sleeve 54 in the first sleeve position.

Movement of the shaft 46 from the first shaft position to the second shaft position results in movement of the contactable component 56 from the first component position to the second component position, thus also resulting in movement of the sleeve 54 from the first sleeve position to the second sleeve position. In the first sleeve position, the sleeve 54 does not interact with the first one-way clutch 28, thus permitting rotation of the second component 24 relative to the first component 22 in the first rotational direction RD1. In the second sleeve position, the sleeve 54 interacts with the first one-way clutch 28, thus preventing rotation of the second component 24 relative to the first component 22 in the first rotational direction RD1 and positionally locking the second component 24 relative to the first component 22. As such, it is to be appreciated that the first sleeve position of the sleeve 54 is associated with the locking mechanism 32 in the first position and the second sleeve position of the sleeve 54 is associated with the locking mechanism 32 in the second position.

The shaft 46 may define a second groove 66, and the locking mechanism 32 may further include a second sleeve 68 disposed between the shaft 46 and the second one-way clutch 30. The locking mechanism 32 may further include a second contactable component 70 moveable between a first component position and a second component position. In the first component position, the second contactable component 70 is disposed at least partially in the second groove 66 of the shaft 46 such that the second one-way clutch 30 permits rotation of the second component 24 in the second rotational direction RD2. In the second component position, the second contactable component 70 is in contact with the second sleeve 68 such that the second one-way clutch 30 prevents rotation of the second component 24 in the second rotational direction RD2.

The second sleeve 68 may be moveable between a first sleeve position associated with the second contactable component 70 in the first component position and a second sleeve position associated with the second contactable component 70 in the second component position. The second sleeve position may be spaced radially outward from the first sleeve position. In other words, the second sleeve 68 in the second sleeve position may be spaced radially outward from the second sleeve 68 in the first sleeve position. Furthermore, the second sleeve 68 may be in contact with the second one-way clutch 30 in the second sleeve position. Contact between the second sleeve 68 and the second one-way clutch 30 assists in preventing rotation of the second component 24.

Moreover, the second sleeve 68 may have a first sleeve portion 62 and a second sleeve portion 64. The first sleeve portion 62 and the second sleeve portion 64 of the second sleeve 68 may be separate components. The first sleeve portion 62 and the second sleeve portion 64 of the second sleeve 68 may both extend approximately halfway circumferentially about the axis A1. In a non-limiting example, the first sleeve portion 62 and the second sleeve portion 64 of the second sleeve 68 may be separated from one another by one or more gaps in the second sleeve position, and the first sleeve portion 62 and the second sleeve portion 64 of the second sleeve 68 may be in contact with one another in the first sleeve position. The gaps between the first sleeve portion 62 and the second sleeve portion 64 of the second sleeve 68 may result in the second sleeve 68 in the second sleeve position being spaced radially outward from the second sleeve 68 in the first sleeve position.

Movement of the shaft 46 from the first shaft position to the second shaft position results in movement of the second contactable component 70 from the first component position to the second component position, thus also resulting in movement of the second sleeve 68 from the first sleeve position to the second sleeve position. In the first sleeve position, the second sleeve 68 does not interact with the second one-way clutch 30, thus permitting rotation of the second component 24 relative to the first component 22 in the second rotational direction RD2. In the second sleeve position, the second sleeve 68 interacts with the second one-way clutch 30, thus preventing rotation of the second component 24 relative to the first component 22 in the second rotational direction RD2 and positionally locking the second component 24 relative to the first component 22. As such, it is to be appreciated that the first sleeve position of the second sleeve 68 is associated with the locking mechanism 32 in the first position and the second sleeve position of the second sleeve 68 is associated with the locking mechanism 32 in the second position.

As shown in FIGS. 4-6, the joint 26 may include a first joint section 72 extending partially about the axis A1. The first joint section 72 is moveable between an open joint position such that the locking mechanism 32 is in the first position and a closed joint position such that the locking mechanism 32 is in the second position. The open joint position is shown in FIG. 4 and the closed joint position is shown in FIGS. 5 and 6. The first joint section 72 in the closed joint position may be in contact with the first plurality of moveable members 40 of the first one-way clutch 28 and may be in contact with the second plurality of moveable members 44 of the second one-way clutch 30. The locking mechanism 32 may further include a latch 74 to hold the first joint section 72 in the closed joint position such that the locking mechanism 32 is held in the second position.

Although not required, the joint 26 may also include a second joint section 76 extending partially about the axis A1. The second joint section 76 is moveable between the open joint position such that the locking mechanism 32 is in the first position and the closed joint position such that the locking mechanism 32 is in the second position. The second joint section 76 in the closed joint position may be in contact with the first plurality of moveable members 40 of the first one-way clutch 28 and may be in contact with the second plurality of moveable members 44 of the second one-way clutch 30. The latch 74 of the locking mechanism 32 may be configured to hold the second joint section 76 in the closed joint position such that the locking mechanism 32 is held in the second position.

The support arm 20 may further include a support structure 78 extending along the axis A1 and fixed relative to one of the first component 22 and the second component 24. In other words, the support structure 78 may be fixed relative to the first component 22 or may be fixed relative to the second component 24. The support structure 78 may be integral with one of the first component 22 and the second component 24. In other words, the support structure 78 may be integral with the first component 22 or the support structure 78 may be integral with the second component 24.

Moreover, the first race 38 of the first one-way clutch 28 may be fixed relative to the support structure 78, may be fixed relative to the first component 22, or may be fixed relative to the second component 24. The first race 38 of the first one-way clutch 28 may be fixed to the other of the first component 22 and the second component 24 that the support structure 78 is fixed to. In other words, in the aspects where the support structure 78 is fixed to the first component 22, the first race 38 may be fixed relative to the second component 24. Alternatively, in the aspects where the support structure 78 is fixed to the second component 24, the first race 38 may be fixed relative to the first component 22.

Additionally, the second race 42 of the second one-way clutch 30 may be fixed relative to the support structure 78, may be fixed relative to the first component 22, or may be fixed relative to the second component 24. The second race 42 of the second one-way clutch 30 may be fixed to the other of the first component 22 and the second component 24 that the support structure 78 is fixed to. In other words, in the aspects where the support structure 78 is fixed to the first component 22, the second race 42 may be fixed relative to the second component 24. Alternatively, in the aspects where the support structure 78 is fixed to the second component 24, the second race 42 may be fixed relative to the first component 22.

The support arm 20 may further include a first hinge 80 fixed relative to the support structure 78 and the first joint section 72. In other words, the first hinge 80 may be fixed to the support structure 78, the first hinge 80 may be fixed to the first joint section 72, and the first hinge 80 may be configured to permit the first joint section 72 to pivot about the first hinge 80 relative to the support structure 78. Although not required, the support arm 20 may also further include a second hinge 82 fixed relative to the support structure 78 and the second joint section 76. In other words, the second hinge 82 may be fixed to the support structure 78, the second hinge 82 may be fixed to the second joint section 76, and the second hinge 82 may be configured to permit the second joint section 76 to pivot about the second hinge 82 relative to the support structure 78.

In another aspect, as shown in FIGS. 7-10, the support arm 20 may include a first component 22 extending along the axis A1, a second component 24 spaced from the first component 22, and a joint 26 coupled to the first component 22 and positionally supporting the second component 24. The joint 26 has an inner joint surface 34 defining a joint interior 36, and the joint 26 includes a clutch assembly 84 configured to selectively prevent rotation of the second component 24 relative to the first component 22.

Figure 7:
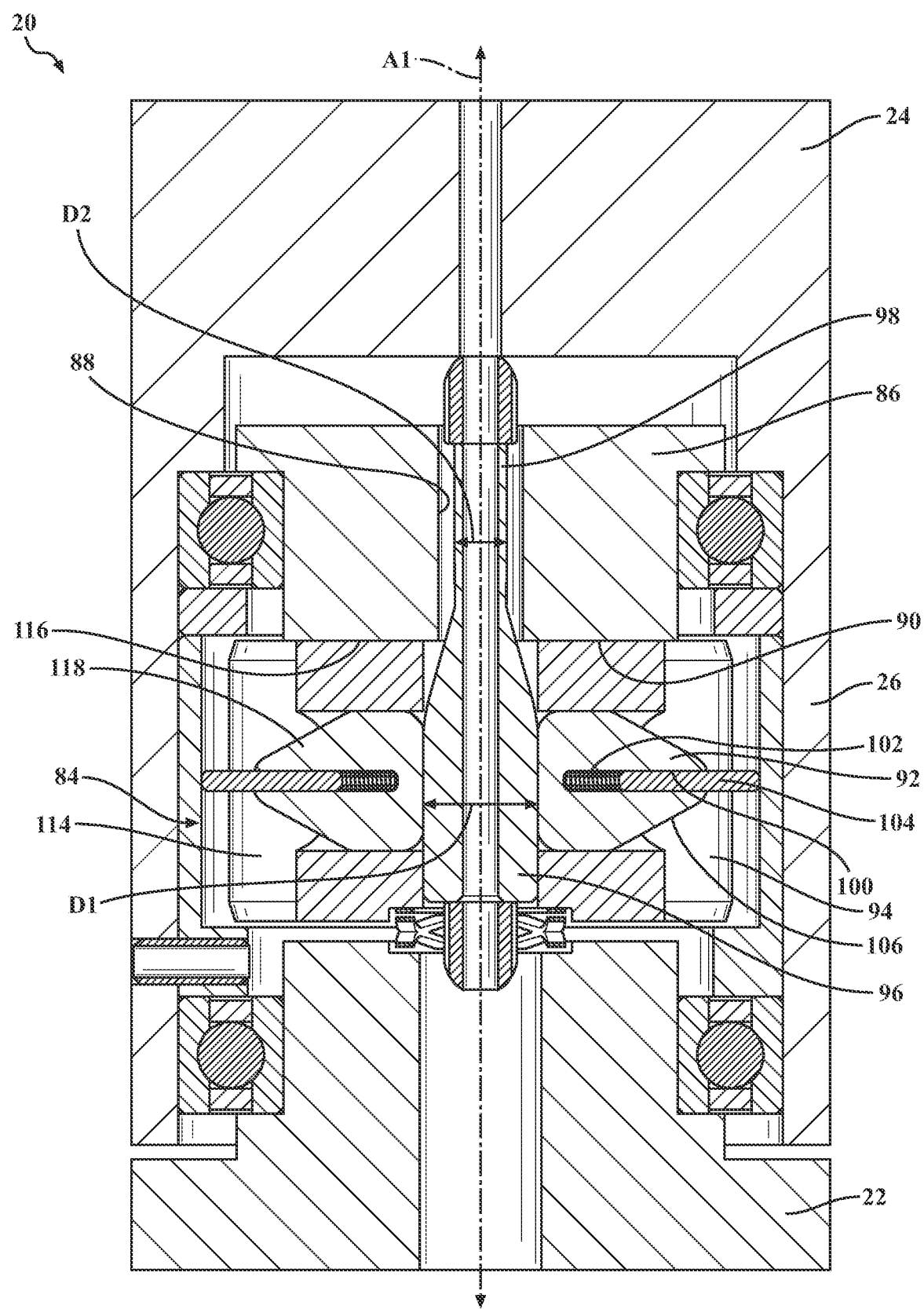
FIG. 7 is a cross-sectional view of yet another implementation of the support arm, with the support arm including a clutch assembly having a shaft in a first shaft position, a plunger in a first plunger position, and a moveable member in a first member position.
Figure 8:
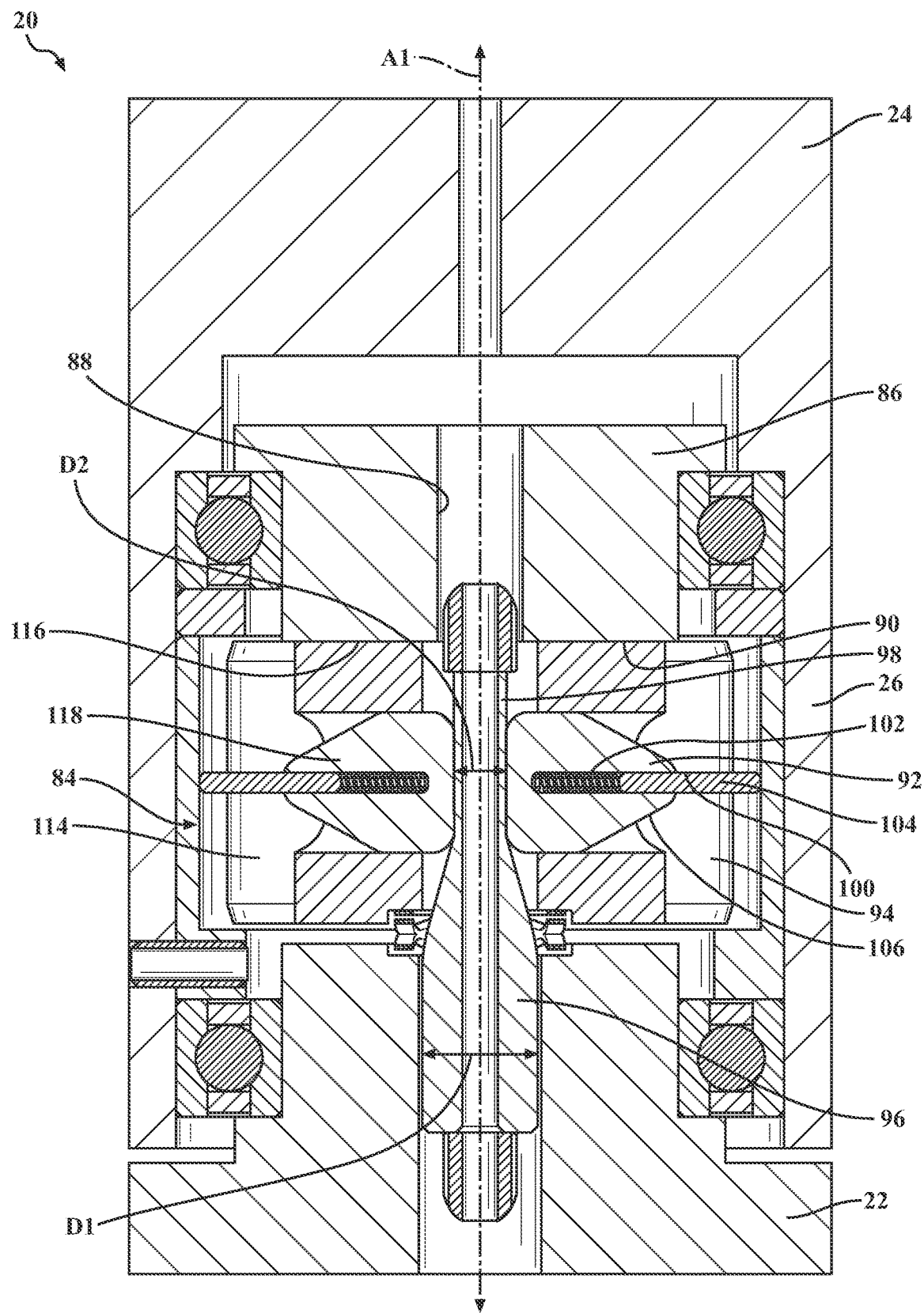
FIG. 8 is a cross-sectional view of the implementation of the support arm shown in FIG. 7, with the clutch assembly including the shaft in a second shaft position, the plunger in a second plunger position, and the moveable member in a second member position.
Figure 9:
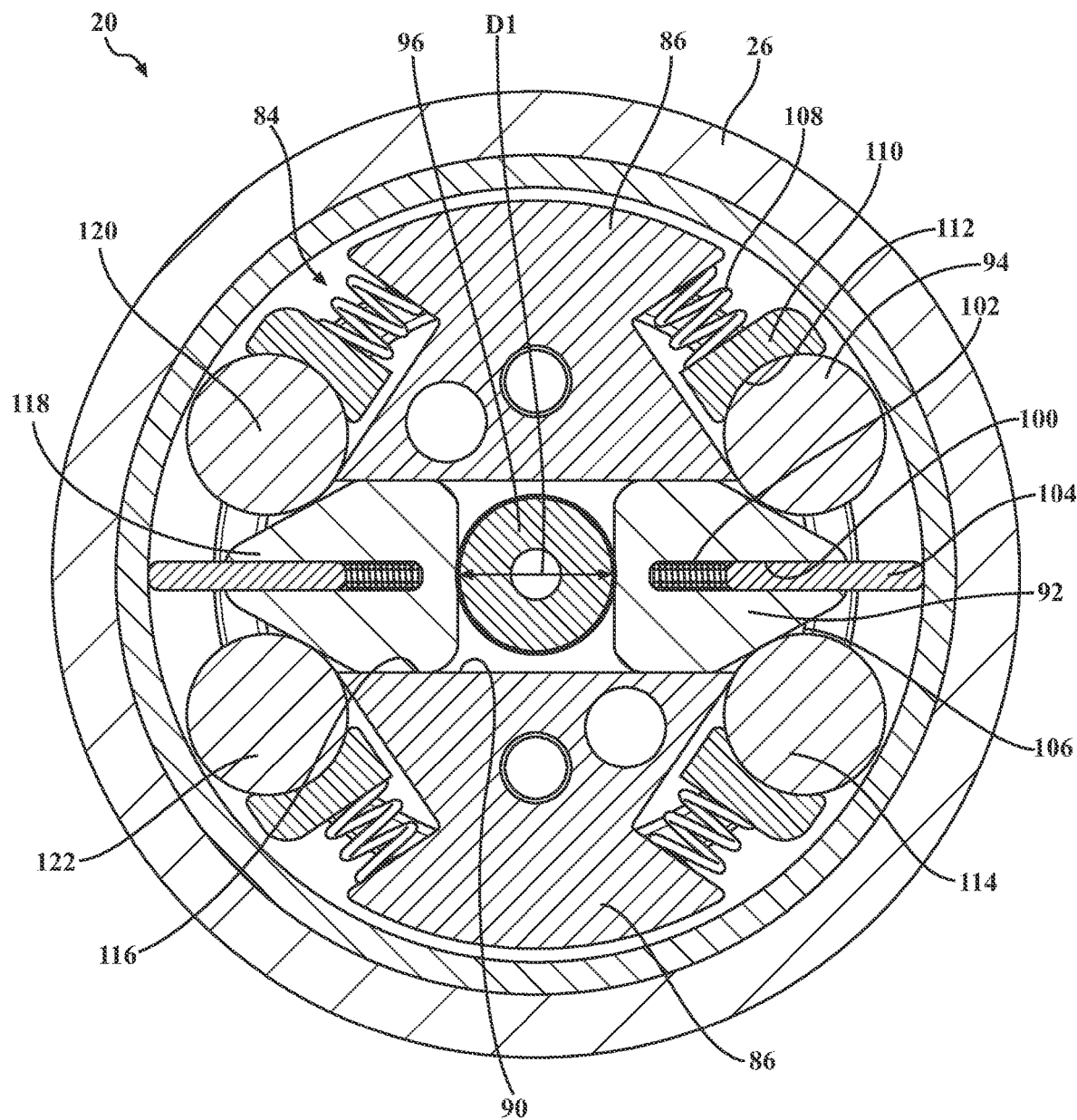
FIG. 9 is a cross-sectional view of the implementation of the support arm shown in FIG. 7, with the clutch assembly including the shaft in the first shaft position, the plunger in the first plunger position, and the moveable member in the first member position.
Figure 10:
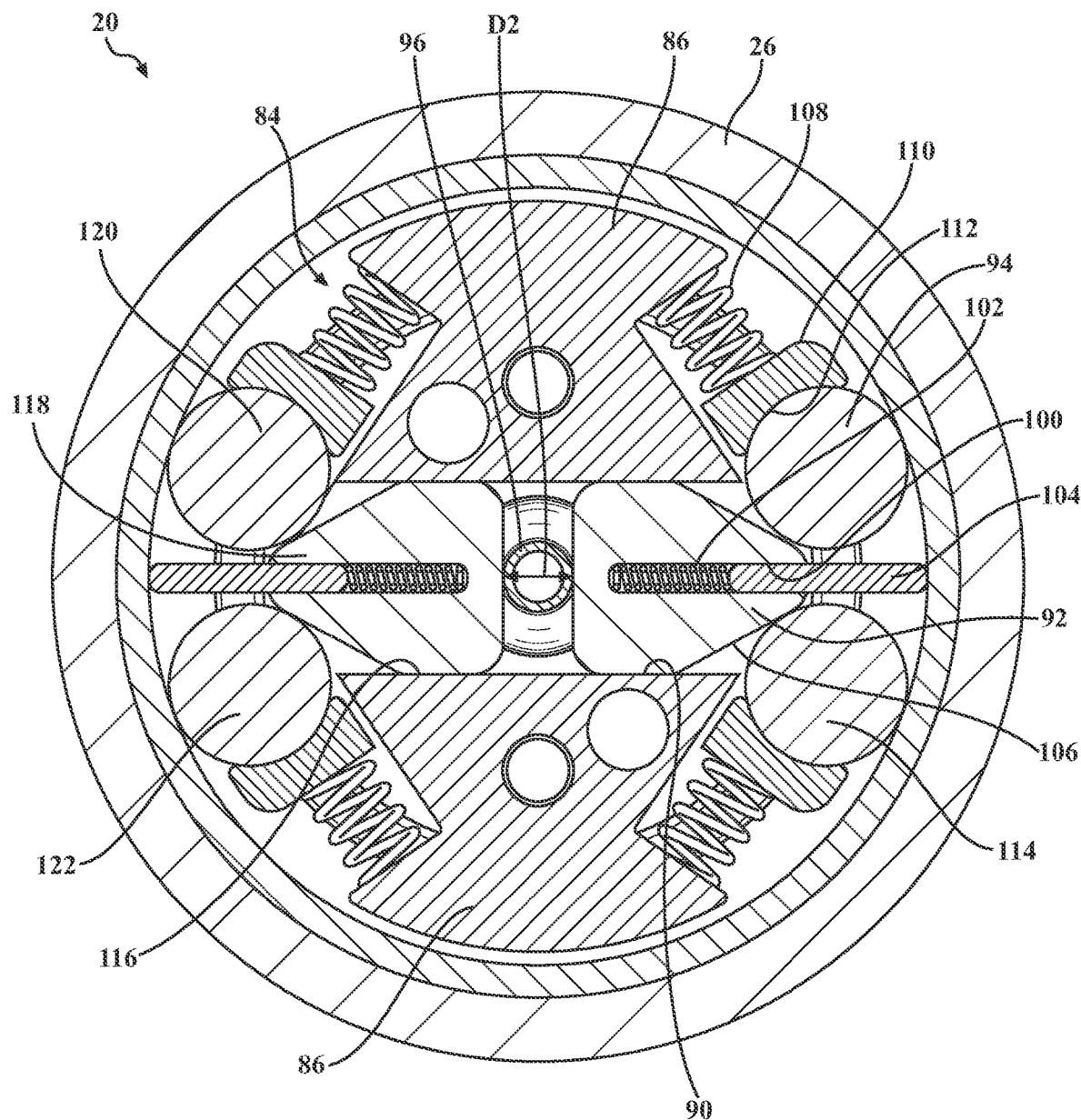
FIG. 10 is a cross-sectional view of the implementation of the support arm shown in FIG. 9, with the clutch assembly including the shaft in the second shaft position, the plunger in the second plunger position, and the moveable member in the second member position.

As shown in FIGS. 7-10, the clutch assembly 84 includes a shaft 46 extending along the axis A1. The shaft 46 is moveable between a first shaft position and a second shaft position spaced from the first shaft position along the axis A1. The first shaft position is shown in FIGS. 7 and 9 and the second shaft position is shown in FIGS. 8 and 10. The clutch assembly 84 also includes a center structure 86 defining a longitudinal bore 88 extending along the axis A1 for receiving the shaft 46. The center structure 86 also defines a transverse bore 90 extending radially away from the axis A1. The clutch assembly 84 further includes a plunger 92 disposed in the transverse bore 90 of the center structure 86. The plunger 92 is moveable between a first plunger position and a second plunger position spaced radially inward from the first plunger position. In other words, the plunger 92 in the second plunger position is spaced radially inward relative to the plunger 92 in the first plunger position. The first plunger position is shown in FIGS. 7 and 9 and the second plunger position is shown in FIGS. 8 and 10.

The clutch assembly 84 further includes a moveable member 94 coupled to the center structure 86. The moveable member 94 is moveable between a first member position associated with the plunger 92 in the first plunger position, and a second member position associated with the plunger 92 in the second plunger position. The first member position is shown in FIGS. 7 and 9 and the second member position is shown in FIGS. 8 and 10. The moveable member 94 is in contact with the inner joint surface 34 of the joint 26 in the second member position to positionally lock the second component 24 relative to the first component 22.

The shaft 46 may have a first shaft portion 96 and a second shaft portion 98 spaced from the first shaft portion 96 along the axis A1. The first shaft portion 96 has a first diameter D1 and the second shaft portion 98 has a second diameter D2. Although not required, the second diameter D2 of the second shaft portion 98 may be less than the first diameter D1 of the first shaft portion 96. The shaft 46 may taper from the first shaft portion 96 to the second shaft portion 98, thus acting as a ramp and permitting a smooth transition between the first shaft position and the second shaft position, between the first plunger position and the second plunger position, and between the first member position and the second member position. Moreover, the first shaft portion 96 of the shaft 46 may be in contact with the plunger 92 in the first plunger position and the second shaft portion 98 of the shaft 46 may be in contact with the plunger 92 in the second plunger position. Said differently, the first shaft portion 96 may be in contact with the plunger 92 when the plunger 92 is in the first plunger position and the second shaft portion 98 may be in contact with the plunger 92 when the plunger 92 is in the second plunger position.

The plunger 92 may define a plunger bore 100, and the clutch assembly 84 may further include a first biasing mechanism 102 disposed in the plunger bore 100. The first biasing mechanism 102 may be a spring, such as but not limited to a wave spring (e.g., a single wave spring, a multiple wave spring), a coil spring (e.g., a compression spring, a helical spring), a disc spring (e.g., a Belleville spring), a conical spring, or a slotted disk spring, among other possibilities.

The clutch assembly 84 may also include a dowel 104 coupled to the first biasing mechanism 102. The dowel 104 may extend radially away from the axis A1. The first biasing mechanism 102 may be configured to bias the dowel 104 radially away from the axis A1, and optionally into contact with the inner joint surface 34 of the joint 26 to assist in positioning the plunger 92, to prevent the plunger 92 from damaging the inner joint surface 34 of the joint 26, and to provide resistance as the shaft 46 moves from the second shaft position toward the first shaft position. It is also to be appreciated that the first biasing mechanism 102 and the dowel 104 result in the plunger 92 being normally in the second plunger position, thus also resulting in the moveable member 94 normally being in the second member position to positionally lock the second component 24 relative to the first component 22. Said differently, the first biasing mechanism 102 and the dowel 104 result in the second component 24 being normally locked relative to the first component 22, and an operator is required to move the shaft 46 from the second shaft position toward the first shaft position against the force exerted by the first biasing mechanism 102 on the dowel 104 to reposition the second component 24 relative to the first component 22.

Additionally, as shown in FIGS. 7-10, the plunger 92 may taper radially away from the axis A1. In other words, as the plunger 92 extends radially away from the axis A1, the diameter of the plunger 92 may decrease. Additionally, the plunger 92 may have a tapered surface 106, and the moveable member 94 may contact the tapered surface 106 of the plunger 92 in the first member position to prevent the moveable member 94 from contacting the inner joint surface 34 of the joint 26. Said differently, the moveable member 94 may contact the tapered surface 106 of the plunger 92 when the plunger 92 is in the first member position. The tapered surface 106 may act as a ramp to smoothly transition the moveable member 94 away from the inner joint surface 34 of the joint 26 as the shaft 46 moves from the second position toward the first shaft position.

Further, the clutch assembly 84 may further include a second biasing mechanism 108 configured to bias the moveable member 94 toward the inner joint surface 34 of the joint 26. The second biasing mechanism 108 may be fixed relative to the center structure 86. The clutch assembly 84 may also further include a bearing structure 110 defining a concave recess 112 configured to receive the moveable member 94. The second biasing mechanism 108 may be fixed relative to the bearing structure 110. Moreover, the moveable member 94 may be cylindrical to permit the moveable member 94 to rotate within the concave recess 112 of the bearing structure 110.

Although not required, the clutch assembly 84 may further include a second moveable member 114 coupled to the center structure 86 and moveable between a third member position associated with the plunger 92 in the first plunger position, and a fourth member position associated with the plunger 92 in the second plunger position. The second moveable member 114 is in contact with the inner joint surface 34 of the joint 26 in the fourth member position to positionally lock the second component 24 relative to the first component 22. The first moveable member 94 may prevent rotation of the second component 24 relative to the first component 22 in the first rotational direction RD1, and the second moveable member 114 may prevent rotation of the second component 24 relative to the first component 22 in the second rotational direction RD2.

The center structure 86 may further define a second transverse bore 116 extending radially away from the axis A1, and the clutch assembly 84 may also include a second plunger 118 disposed in the second transverse bore 116 of the center structure 86. The second plunger 118 is moveable between a third plunger position and a fourth plunger position spaced radially inward from the third plunger position. The clutch assembly 84 may further include a third moveable member 120 coupled to the center structure 86 and moveable between a fifth member position associated with the second plunger 118 in the third plunger position, and a sixth member position associated with the second plunger 118 in the fourth plunger position. The third moveable member 120 is in contact with the inner joint surface 34 of the joint 26 in the sixth member position to positionally lock the second component 24 relative to the first component 22.

Further still, the clutch assembly 84 may include a fourth moveable member 122 coupled to the center structure 86 and moveable between a seventh member position associated with the second plunger 118 in the third plunger position, and an eighth member position associated with the second plunger 118 in the fourth plunger position. The fourth moveable member 122 is in contact with the inner joint surface 34 of the joint 26 in the eighth member position to positionally lock the second component 24 relative to the first component 22. The third moveable member 120 may prevent rotation of the second component 24 relative to the first component 22 in the first rotational direction RD1, and the fourth moveable member 122 may prevent rotation of the second component 24 relative to the first component 22 in the second rotational direction RD2.

The invention has been described in an illustrative manner, and it is to be understood that the terminology which has been used is intended to be in the nature of words of description rather than of limitation. Many modifications and variations of the present invention are possible in light of the above teachings, and the invention may be practiced otherwise than as specifically described.

What is claimed is:

1. A support arm comprising:
   a first component extending along an axis;
   a second component spaced from the first component; and
   a joint coupled to the first component and positionally supporting the second component, the joint including,
      a first one-way clutch configured to selectively prevent rotation of the second component relative to the first component in a first rotational direction;
      a second one-way clutch configured to selectively prevent rotation of the second component relative to the first component in a second rotational direction opposite the first rotational direction; and
      a locking mechanism moveable between,
         a first position wherein the first one-way clutch permits rotation of the second component relative to the first component in the first rotational direction and the second one-way clutch permits rotation of the second component relative to the first component in the second rotational direction to allow movement of the second component relative to the first component; and
         a second position wherein the first one-way clutch prevents rotation of the second component relative to the first component in the first rotational direction and the second one-way clutch prevents rotation of the second component relative to the first component in the second rotational direction to positionally lock the second component relative to the first component.

2. The support arm of claim 1, wherein the first one-way clutch and the second one-way clutch are spaced from one another along the axis.

3. The support arm of claim 1, wherein the first one-way clutch and the second one-way clutch are configured to permit the second component to be positionally locked in any rotational orientation relative to the first component.

4. The support arm of claim 1, wherein the first one-way clutch includes a first race and a first plurality of moveable members coupled to the first race, and wherein the second one-way clutch includes a second race and a second plurality of moveable members coupled to the second race.

5. The support arm of claim 4, wherein the first plurality of moveable members are sprags and the second plurality of moveable members are sprags.

6. The support arm of claim 1, wherein the first component is a first link, and the second component is a second link.

7. The support arm of claim 1, wherein the first component is a link, and the second component is at least one chosen from an end effector, a tool, an array, a retractor, and an attachment interface.

8. The support arm of claim 1, wherein at least one of the first component and the second component are disposed at least partially in the joint interior of the joint.

9. The support arm of claim 1, wherein the joint includes a first joint section extending partially about the axis and moveable between an open joint position such that the locking mechanism is in the first position and a closed joint position such that the locking mechanism is in the second position.

10. The support arm of claim 9, wherein the locking mechanism further includes a latch to hold the first joint section in the closed joint position such that the locking mechanism is held in the second position.

11. The support arm of claim 9, further comprising a support structure extending along the axis and fixed relative to one of the first component and the second component, and a first hinge fixed relative to the support structure and the first joint section.

12. The support arm of claim 1, wherein the joint has an inner joint surface defining a joint interior, wherein the first one-way clutch is disposed within the joint interior of the joint, and wherein the second one-way clutch is disposed within the joint interior of the joint.

13. The support arm of claim 12, wherein the locking mechanism further includes a shaft disposed at least partially in the joint interior of the joint, with the shaft moveable along the axis between a first shaft position such that the locking mechanism is in the first position and a second shaft position such that the locking mechanism is in the second position.

14. The support arm of claim 13, wherein the locking mechanism further includes a cable coupled to the shaft, wherein the cable is configured to be manipulated by an operator to linearly translate the shaft from the second shaft position toward the first shaft position.

15. The support arm of claim 13, wherein the locking mechanism further includes a biasing mechanism coupled to the shaft and configured to bias the shaft toward the second shaft position.

16. The support arm of claim 13, wherein the shaft defines a groove, wherein the locking mechanism further includes a sleeve disposed between the shaft and the first one-way clutch, and wherein the locking mechanism further includes a contactable component moveable between,
   a first component position where the contactable component is disposed at least partially in the groove of the shaft such that the first one-way clutch permits rotation of the second component in the first rotational direction, and
   a second component position where the contactable component is in contact with the sleeve such that the first one-way clutch prevents rotation of the second component in the first rotational direction.

17. The support arm of claim 16, wherein the shaft defines a second groove, wherein the locking mechanism further includes a second sleeve disposed between the shaft and the second one-way clutch, and wherein the locking mechanism further includes a second contactable component moveable between,
   a first component position where the second contactable component is disposed at least partially in the second groove of the shaft such that second one-way clutch permits rotation of the second component in the second rotational direction, and
   a second component position where the second contactable component is in contact with the second sleeve such that the second one-way clutch prevents rotation of the second component in the second rotational direction.

18. The support arm of claim 16, wherein the sleeve is moveable between,
   a first sleeve position associated with the contactable component in the first component position, and a second sleeve position associated with the contactable component in the second component position, wherein the second sleeve position is spaced radially outward from the first sleeve position.

19. The support arm of claim 18, wherein the sleeve is in contact with the first one-way clutch in the second sleeve position.

20. A joint for a support arm, the joint comprising:
a first one-way clutch extending about an axis and configured to selectively prevent rotation of a second component relative to a first component in a first rotational direction;
a second one-way clutch spaced from the first one-way clutch along the axis, the second one-way clutch configured to selectively prevent rotation of the second component relative to the first component in a second rotational direction opposite the first rotational direction; and
a locking mechanism moveable between,
  a first position where the first one-way clutch is configured to permit rotation of the second component relative to the first component in the first rotational direction and the second one-way clutch is configured to permit rotation of the second component relative to the first component in the second rotational direction to allow movement of the second component relative to the first component; and
  a second position where the first one-way clutch is configured to prevent rotation of the second component relative to the first component in the first rotational direction and the second one-way clutch is configured to prevent rotation of the second component relative to the first component in the second rotational direction to positionally lock the second component relative to the first component.

21. A surgical support arm comprising:
a link extending along an axis;
a surgical instrument; and
a joint coupled to the link and positionally supporting the surgical instrument, the joint including,
  a first one-way clutch configured to selectively prevent rotation of the surgical instrument relative to the link in a first rotational direction;
  a second one-way clutch configured to selectively prevent rotation of the surgical instrument relative to the link in a second rotational direction opposite the first rotational direction; and
  a locking mechanism moveable between,
    a first position wherein the first one-way clutch permits rotation of the surgical instrument relative to the link in the first rotational direction and the second one-way clutch permits rotation of the surgical instrument relative to the link in the second rotational direction to allow movement of the surgical instrument relative to the link; and
    a second position wherein the first one-way clutch prevents rotation of the surgical instrument relative to the link in the first rotational direction and the second one-way clutch prevents rotation of the surgical instrument relative to the link in the second rotational direction to positionally lock the surgical instrument relative to the link.

\* \* \* \* \*